(12) United States Patent
Boday et al.

(10) Patent No.: US 10,604,539 B2
(45) Date of Patent: *Mar. 31, 2020

(54) SULFUR SCAVENGING MATERIALS

(71) Applicant: International Business Machines Corporation, Armonk, NY (US)

(72) Inventors: Dylan J. Boday, Tucson, AZ (US); Jeannette M. Garcia, San Leandro, CA (US); James L. Hedrick, Pleasanton, CA (US); Rudy J. Wojtecki, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/240,493

(22) Filed: Jan. 4, 2019

(65) Prior Publication Data

US 2019/0135839 A1  May 9, 2019

Related U.S. Application Data

(62) Division of application No. 15/158,356, filed on May 18, 2016, now abandoned, which is a division of application No. 14/294,220, filed on Jun. 3, 2014, now Pat. No. 9,469,660.

(51) Int. Cl.

| | |
|---|---|
| *C07F 7/02* | (2006.01) |
| *C08K 5/54* | (2006.01) |
| *B01D 53/14* | (2006.01) |
| *B01J 20/28* | (2006.01) |
| *B01J 20/22* | (2006.01) |
| *B01D 53/02* | (2006.01) |
| *C08K 5/3492* | (2006.01) |
| *C07F 7/18* | (2006.01) |
| *C07D 251/24* | (2006.01) |
| *C07F 7/08* | (2006.01) |
| *C02F 1/28* | (2006.01) |
| *B01D 53/48* | (2006.01) |
| *B01J 20/32* | (2006.01) |
| *B01D 39/04* | (2006.01) |
| *B01D 53/50* | (2006.01) |
| *B01D 53/82* | (2006.01) |
| *C02F 103/36* | (2006.01) |
| *C02F 101/10* | (2006.01) |
| *C02F 103/10* | (2006.01) |

(52) U.S. Cl.
CPC .............. *C07F 7/025* (2013.01); *B01D 39/04* (2013.01); *B01D 53/02* (2013.01); *B01D 53/48* (2013.01); *B01D 53/508* (2013.01); *B01D 53/82* (2013.01); *B01J 20/22* (2013.01); *B01J 20/28016* (2013.01); *B01J 20/28019* (2013.01); *B01J 20/3255* (2013.01); *C02F 1/288* (2013.01); *C07D 251/24* (2013.01); *C07F 7/0836* (2013.01); *C07F 7/1804* (2013.01); *C08K 5/3492* (2013.01); *B01D 2253/106* (2013.01); *B01D 2253/20* (2013.01); *B01D 2253/25* (2013.01); *B01D 2253/304* (2013.01); *B01D 2257/30* (2013.01); *B01D 2257/304* (2013.01); *B01D 2257/306* (2013.01); *C02F 1/285* (2013.01); *C02F 2101/101* (2013.01); *C02F 2103/10* (2013.01); *C02F 2103/365* (2013.01); *C02F 2303/08* (2013.01); *Y10T 428/2982* (2015.01); *Y10T 428/2991* (2015.01); *Y10T 428/2993* (2015.01); *Y10T 428/2995* (2015.01)

(58) Field of Classification Search
CPC ...... C07F 7/025; C08K 5/544; B01D 53/1456
USPC .................................. 544/180; 428/403–407
See application file for complete search history.

(56) References Cited

U.S. PATENT DOCUMENTS

| | | | |
|---|---|---|---|
| 2,889,277 | A | 6/1959 | Hughes |
| 3,173,799 | A | 3/1965 | George |
| 3,340,232 | A | 9/1967 | Smith et al. |
| 3,598,748 | A | 8/1971 | Hirosawa |
| 3,915,970 | A | 10/1975 | Limaye et al. |
| 3,957,742 | A | 5/1976 | Kveton |

(Continued)

FOREIGN PATENT DOCUMENTS

| | | |
|---|---|---|
| CN | 101265255 A | 9/2008 |
| EP | 2636697 A1 | 9/2013 |

(Continued)

OTHER PUBLICATIONS

Amosa et al., Sulphide Scavengers in Oil and Gas Industry—A Review, NAFTA 61 (2) 85-92 (2010).

D.R. Anderson et al., Thermally resistance polymers containing the S-triazine ring, Journal of Polymer Science Part A-1: PolymerO;emistry, vol. 4, Issue 7, pp. 1689-1702.

(Continued)

*Primary Examiner* — Venkataraman Balasubramanian
(74) *Attorney, Agent, or Firm* — Patterson + Sheridan, LLP

(57) ABSTRACT

Materials which react with ("scavenge") sulfur compounds, such as hydrogen sulfide and mercaptans, are useful for limiting sulfur-induced corrosion. Surface-modified particles incorporating a hexahydrotriazine moiety are disclosed and used as sulfur scavengers. These surface-modified particles are used a filter media in fixed filter systems and as additives to fluids including sulfur compounds. The hexahydrotriazine moiety can react with sulfur compounds in such a manner as to bind sulfur atoms to the surface-modified particles, thus allowing removal of the sulfur atoms from fluids such as crude oil, natural gas, hydrocarbon combustion exhaust gases, sulfur polluted air and water. The surface-modified particles may, in general, be sized to allow separation of the particles from the process fluid by sedimentation, size-exclusion filtration or the like.

20 Claims, 8 Drawing Sheets

(56) References Cited

U.S. PATENT DOCUMENTS

| | | |
|---|---|---|
| 4,010,028 A | 3/1977 | Irwin, Sr. et al. |
| 4,106,904 A | 8/1978 | Oude Alink et al. |
| 4,224,417 A | 9/1980 | Hajek et al. |
| 4,225,481 A | 9/1980 | Wagner |
| 4,246,160 A | 1/1981 | Wagner et al. |
| 4,301,262 A | 11/1981 | Wagner et al. |
| 4,674,377 A | 6/1987 | Groth |
| 4,874,858 A | 10/1989 | Magistro |
| 4,877,451 A | 10/1989 | Winnik et al. |
| 4,978,512 A | 12/1990 | Dillon |
| 5,112,796 A | 5/1992 | Iannicelli |
| 5,554,349 A | 9/1996 | Rivers et al. |
| 5,674,377 A | 10/1997 | Sullivan, III et al. |
| 5,830,243 A | 11/1998 | Wolak et al. |
| 7,004,333 B2 | 2/2006 | Marcotullio et al. |
| 7,384,434 B2 | 6/2008 | Malfer et al. |
| 9,469,660 B2 * | 10/2016 | Boday .............. B01J 20/28019 |
| 9,592,470 B2 | 3/2017 | Boday et al. |
| 9,610,353 B2 | 4/2017 | Aviv et al. |
| 9,610,535 B2 | 4/2017 | Boday et al. |
| 2009/0037018 A1 | 2/2009 | Saikawa et al. |
| 2009/0039018 A1 | 2/2009 | Jordi et al. |
| 2009/0076198 A1 | 3/2009 | Giesenberg et al. |
| 2009/0181240 A1 | 7/2009 | Williams et al. |
| 2010/0107476 A1 | 5/2010 | Cosimbescu |
| 2012/0049308 A1 | 3/2012 | Nishimura et al. |
| 2013/0192739 A1 | 8/2013 | Boday et al. |
| 2014/0171721 A1 | 6/2014 | Bertrand, III |
| 2015/0343352 A1 | 12/2015 | Boday et al. |
| 2015/0343421 A1 | 12/2015 | Boday et al. |
| 2015/0353584 A1 | 12/2015 | Boday et al. |
| 2015/0360173 A1 | 12/2015 | Boday et al. |

FOREIGN PATENT DOCUMENTS

| | | |
|---|---|---|
| GB | 928112 A | 6/1963 |
| GB | 1531578 A | 11/1978 |
| WO | 0166614 A2 | 9/2001 |
| WO | 0198388 A1 | 12/2001 |
| WO | 0226849 A1 | 4/2002 |
| WO | 2015187705 A1 | 12/2015 |

OTHER PUBLICATIONS

Elbert, et al. "Conjugate Addition Reactions Combined with Free-Radical Cross-Linking for the Design of Materials for Tissue Engineering," Biomacromolecules 2001, 2, 430-441; Published on Web Mar. 3, 2001.

Fabian Suriano et al., Functionalized cyclic carbonates: from synthesis and metal-free catalyzed ring-openign polymerization to applications, Polymer Chemsitry, The Royal Society of Chemistry, 2011, Accepted Aug. 13, 2010, pp. 528-533.

Farrar, "Reactions of Formaldehyde With Aromatic Amines," J. Appl. Chem, 14, 1964, 389-399.

Geng, et al., "Nanoindentation behavior of ultrathin polymeric films," Polymer 46 (2005) 11768-11772; Available online Oct. 19, 2005.

Hemant S. Patel et al., Studies on Synthesis an Characterization of some Novel Aromatic Copolyesters based on s-Traizine, Iranian Polymer Journal, vol. 14, No. 12, 2005, pp. 1090-1098.

Henri Ulrich et al., Reaction of Chloromethyl Ether with Primary Amines, May 1961, pp. 1637-1638.

Hiller, et al., "Laser-engravable hexahydrotriazine polymer networks," Mat Res Innovat (2002) 6: 179-184.

Hydrogen Sulfide Management. Mitigation options in petroleum refining, storage and transportation, White Paper, Baker Hughes, pp. 1-12.

Jeanette M. Garcia et al., Recyclable, Strong Thermosets and Organogels via Paraformaldehyde Condensation with Diamines, Science AAAS, vol. 344, May 16, 2014, pp. 732-735.

John Markoff, Error at IBM Lap Finds New Family of Materials, New York Times, May 15, 2014, 4 pages.

National Institute of Standards and Technology. Benzenamine, 4-bromo-N, N-dimethyl-. [online]. [retrieved on Jul. 24, 2015]. Retrieved from the Internet <URL: http://webbook.nist.gov/cgi/cbook.cgi?ID=586-77-6&Units=SI>, 2011 p. 1.

Oliver, et al. "Measurement of hardness and elastic modulus by; instrumented indentation: Advances in understanding and; refinements to methodology," J. Mater. Res., vol. 19, No. 1, Jan. 2004, 3-20.

PCT International Search Report and Writen Opinion for Application No. PCT/US15/33800 dated Aug. 21, 2015.

Raquel Lebrero et al., Odor abatement in biotrickling filters: Effect of the EBRT on methyl mercaptan and hydrophobic voes removal, Bioresource Technology, Special Issue: Innovative Researches on Algal Biomass, vol. 109, Apr. 2012, pp. 38-45.

Wang Yulan et al., Synthesis and Properties of Poly-1, 3, 5-Triazines, Polymer Communications, No. 2, 1984, pp. 117-123.

Singh, et al., "Ultrasound mediated Green Synthesis of Hexa-hydro Triazines," J. Mater. Environ. Sci. 2 (4) (2011) 403-406.

Stafford, et al., "A buckling-based metrology for measuring; the elastic moduli of polymeric thin films," Nature Materials_Aug. 3, 2004, 545-550; Published online: Jul. 11, 2004.

T. Okita, Filter method for the determination of trace quantities of amines, mercaptans, and organic sulphides in the atmosphere, Atmospheric Environment (1967), vol. 4, Issue 1, Jan. 1970, pp. 93-102.

IBM, "List of IBM Patents or Patent Applications Treated as Related," for U.S. Appl. No. 16/240,493 tilted "Sulfur Scavenging Materials," filed Jan. 4, 2019.

* cited by examiner

SULFUR SCAVENGING MATERIALS

This application is a divisional of co-pending U.S. patent application Ser. No. 15/158,356, filed May 18, 2016, which is a divisional of U.S. patent application Ser. No. 14/294,220, filed Jun. 3, 2014, now U.S. Pat. No. 9,469,660. The aforementioned related patent applications are herein incorporated by reference in their entirety.

BACKGROUND

The present disclosure relates to materials that react with sulfur and sulfur-containing compounds, and more specifically to filtration and removal of sulfur and sulfur-containing compounds from fluids.

Sulfur and sulfur-containing compounds are often unwanted impurities in a variety of contexts. For example, sulfur is typically the most abundant element after carbon and hydrogen in crude oil. Sulfur in crude oil may be in the form of hydrogen sulfide ($H_2S$) and/or thiols (also referred to as mercaptans). These sulfur compounds, particularly $H_2S$, may cause corrosion of metal pipeline components, storage tanks, and processing equipment. Additionally, any sulfur that remains in end-use fuels and lubricants may cause corrosion of, or other damage to, end-user equipment (e.g., engines, boilers, bearings, etc.). Combusted fuels or materials that include sulfur ultimately contribute to pollution as sulfur oxides ($SO_x$). Sulfur oxides cause harmful environmental effects and are particularly significant as contributors to air pollution. The various sulfur compounds emitted into the environment may corrode unprotected materials and be harmful to human health.

A need exists for materials and methods for removing sulfur and sulfur-containing compounds from a fluid or otherwise protecting materials against corrosion caused by sulfur and sulfur-containing compounds.

SUMMARY

In an embodiment of the disclosure, a surface-modified particle including a hexahydrotriazine moiety linked via covalent bonds to the particle is described. The surface modified-particle may, in some embodiments, be used in processes and apparatuses for removal of sulfur compounds from fluids.

In another embodiment of the disclosure, a method of making a surface-modified particle is described. The method includes exposing an inorganic particle having a hydroxyl reaction site thereon to a silane including a primary amine group and exposing the inorganic particle to an aniline compound. In an exemplary embodiment, the method produces a surface-modified particle including a hexahydrotriazine moiety linked via covalent bonds to the particle.

In yet another embodiment of the disclosure, a method of removing a sulfur compound from a fluid is disclosed. The method includes placing a fluid including a sulfur compound in contact with a particle having a hexahydrotriazine moiety linked via covalent bonds thereto.

Fluids in this context may include, without limitation, liquids, gases, and mixed-phase flows, streams, solutions, mixtures, and suspensions. Sulfur compounds in this context includes, without limitation, hydrogen sulfide ($H_2S$), thiols (R—SH, where R includes at least one carbon), and sulfur allotropes (e.g., "octosulfur" ($S_8$)). Aniline compounds in this context includes, without limitation, amino-aromatic compounds. Amino-aromatic compounds in this context includes, without limitation, such molecules as aniline ($C_6H_5NH_3$) and N,N-dimethyl-p-phenylenediamine.

The above-described embodiments and other features and advantages of the present disclosure will be appreciated and understood by those skilled in the art from the following detailed description, drawings, and appended claims

DETAILED DESCRIPTION

Small molecule compounds including, for example, triazine groups have been used as sulfur scavengers in crude oil production and refining applications. In general, while these small molecule compounds may react with sulfur compounds, such as $H_2S$, in the process fluid (e.g., crude oil), additional process steps are often required to remove the sulfur-reacted small molecule compounds (and also possibly any remaining, un-reacted small molecule compound) from the process fluid. Typically, these additional processing steps are energy intensive, complex, and/or costly. For example, distillation or solvent extraction methods may be used to separate the spent scavenger molecules from the process fluid. It would be desirable to provide materials and methods for removing sulfur compounds which would not require distillation or solvent extraction processes to separate spent and un-reacted sulfur scavenger molecules from the process fluid.

Figure 1:
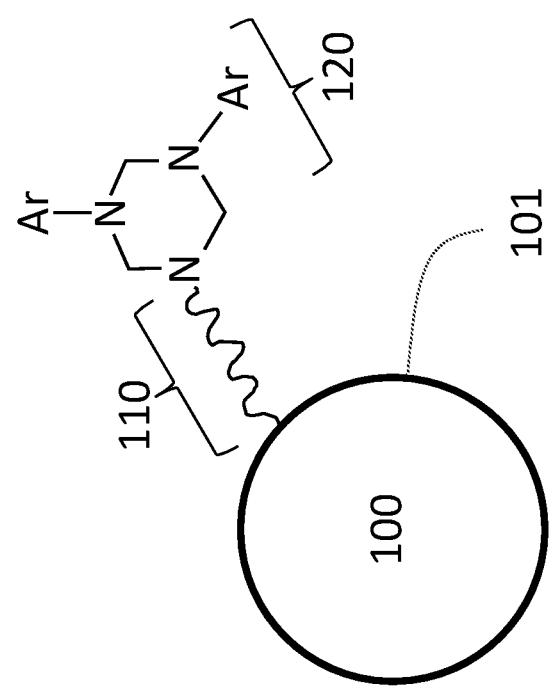
FIG. 1 depicts a surface-modified particle having a moiety that reacts with sulfur compounds.

FIG. 1 depicts a surface-modified particle having a moiety that reacts with sulfur compounds according to an embodiment of the present disclosure. In FIG. 1, particle 100 has a sulfur-reactive moiety 120 attached to a surface 101 thereof via a linkage 110.

In an embodiment, particle 100 is a silica ($SiO_2$) particle, but in other embodiments particle 100 may comprised of other inorganic materials, including without limitation, glasses, ceramics, metal oxides, and the like. Particle 100 may specifically comprise alumina ($Al_2O_3$) in some embodiments, for example. Particle 100 may comprise cellulose or cellulosic material in some embodiments. Particle 100 may be comprised of a coated core or an interior of a first material and a surface coating comprising a second material or a surface treated to provide reactive sites for linkage of the sulfur-reactive moiety 120 to the first material.

Particle 100 is depicted as having a spherical shape, but in general any shape may be adopted. For example, particle 100 may be spherical, rod-like, disk-shaped, plate-shaped, ring-shaped, pipe-shaped, or irregular-shaped, without limitation. Particle 100 may also have various pores, pits, or channels in its outer surface 101. Such pores, pits, or channels may be regularly arrayed on outer surface 101 in specific patterns or may be randomly disposed.

Particle 100 may be a portion of a coating or incorporated into a coating of a surface or a substrate. In some embodiments, particle 100 may be a substrate having, or being treated to have, reactive sites (i.e., reactive with respect to a silane including a primary amine group). A substrate in this context may be, for example, an interior surface of a pipe, an exterior surface of a pipe, a countertop, a surface of a storage tank, a microelectronic component, a silicon wafer, a printed circuit board, or portions of the foregoing.

In an embodiment, particle 100 may be a nano-scale particle (1 nm-1000 nm), however, in general, the particle 100 may be any of dimension (e.g., 1 nanometer (nm)-1000 millimeter (mm)) including macroscopic dimensions.

Linkage 110 connects sulfur-reactive moiety 120 to surface 101 of particle 100. In an embodiment, linkage 110 is formed using an aminosilane compound. Linkage 110 may, for example, include an alkyl chain having 2 to 12 carbons or an aromatic linker. The alkyl chain may have one or more substituents attached thereto in addition to sulfur-reactive moiety 120. Linkage 110 could include a siloxane, an ether, a sulfone, an ester, a carbonate, and/or an amide group in polymeric, oligomeric, or otherwise, form. In some embodiment, linkage 110 may comprise a siloxane chain or a poly(ethylene glycol) ether-type (PEG-ether) chain.

In an example embodiment, linkage 110 may be formed using (3-aminopropyl)triethoxysilane (APTES). In general, when particle 100 is silica the surface 101 will include silanol (—Si—OH) groups generated by reaction of atmospheric moisture with exposed silicon atoms. A reaction between a silane group and a surface 101 silanol group can be used to covalently bond the silicon atom of the aminosilane compound to particle 100. The amino group of the aminosilane compound can be used to provide the sulfur-reactive moiety 120.

Sulfur-reactive moiety 120 includes a trivalent hexahydrotriazine group corresponding to formula (1):

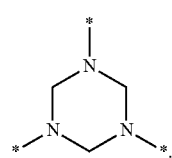

(1)

The substituents labeled "Ar" in FIG. 1 are aryl groups, for example. Without limitation, the "Ar" groups may correspond to a phenyl group or a N,N-dimethylamino-p-phenyl group. In general "Ar," may correspond to any electron-donating group, such as without limitation, methyl ether (OMe), pyrene, aromatics, —OH (hydroxyl), —SH (sulfhydryl), —S—R (alkylthio, wherein R includes an alkyl group).

Figure 2:
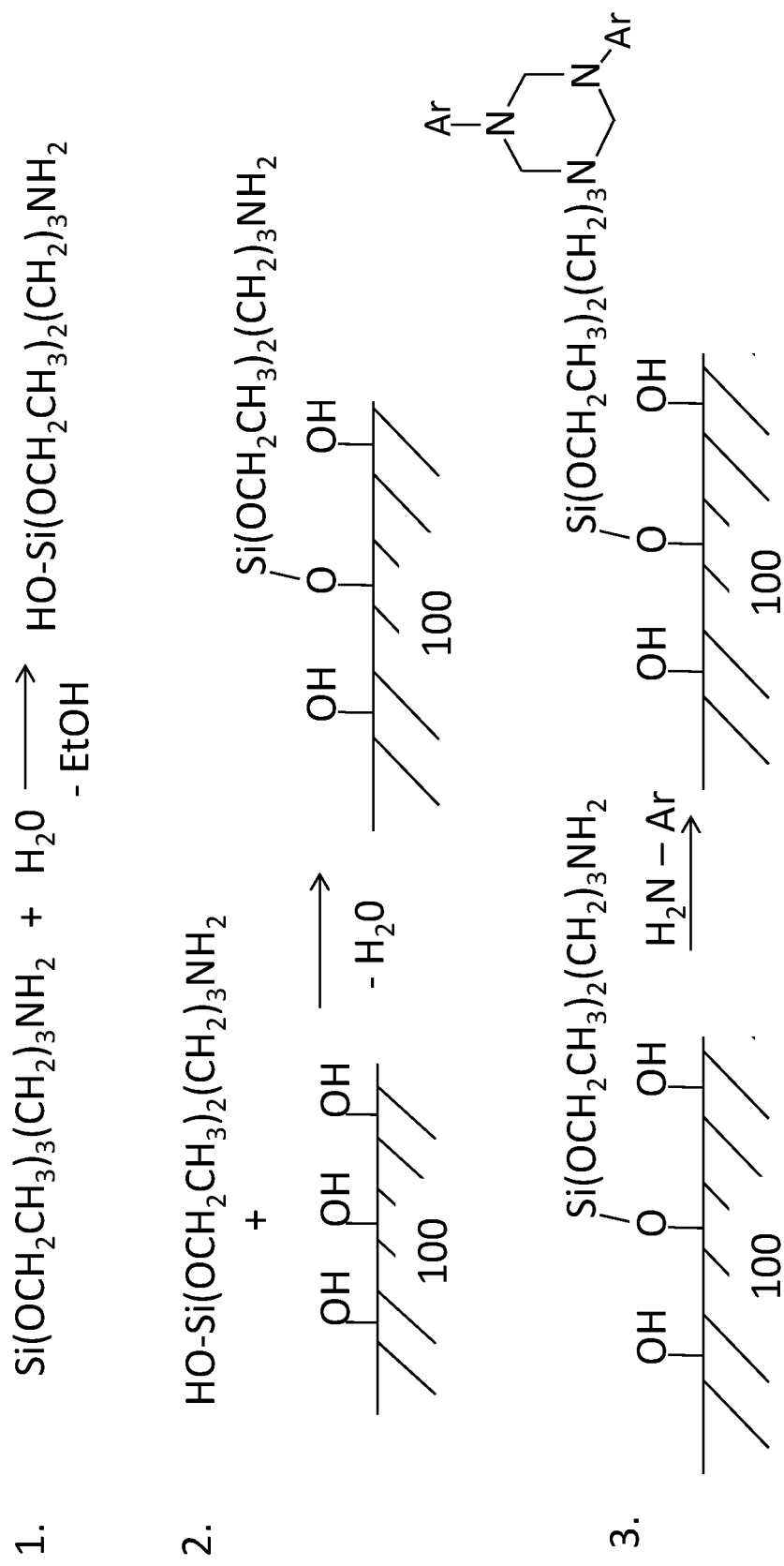
FIG. 2 depicts an exemplary reaction scheme for producing a surface-modified particle having a moiety that reacts with sulfur compounds.

FIG. 2 depicts an exemplary reaction scheme for producing a surface-modified particle having a moiety that reacts with sulfur compounds. A particle 100 has various —OH reaction sites on surface 101. When particle 100 is silica, particle 100 may be purposively exposed to water to promote the formation of the —OH reaction sites, though typically mere exposure to normal atmospheric humidity will generate potential —OH reaction sites on silica surfaces. When the particle 100 is exposed to an aminosilane compound (e.g., APTES), the aminosilane compound reacts with the —OH reaction site resulting in a covalent bonding of the silicon atom in the aminosilane compound and the oxygen atom of the —OH reaction site. Without being limited to any particular reaction mechanism, FIG. 2 depicts the reaction between APTES and the —OH reaction site as going through a silanol intermediary. Such intermediary maybe be formed as distinct species or may be transitory. The intermediary may be formed in solution phase or at the surface of particle 100. After reaction with the aminosilane, particle 100 has an amino-functionalized compound attached to surface 101.

While a single —OH reaction on particle 100 is depicted as reacted in FIG. 2, many —OH reaction sites on particle 100 may ultimately react with available aminosilane compounds such that substantial portion of surface 101 may be covered with covalently bonded amino groups.

In an example embodiment, sulfur-reactive moiety 120 may be formed in a reaction between amino-functionalized particle 100 and aniline ($C_6H_5NH_2$). The reaction between aniline and the primary amine group attached to particle 100 produces a hexahydrotriazine group attached to particle 100. Sulfur-reactive moiety 120 may also be formed in a reaction between the amino-functionalized particle and N,N-dimethyl-p-phenylenediamine (DPD) corresponding to formula (2):

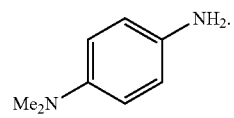

(2)

Other examples of an aniline compound which may be used to form sulfur-reactive moiety 120 include: p-methoxyaniline (MOA), N,N-dimethyl-1,5-diaminonaphthalene (15DMN), N,N-dimethyl-1,4-diaminonaphthalene (14DMN), and N,N-dimethylbenzidene (DMB), which have the following structures:

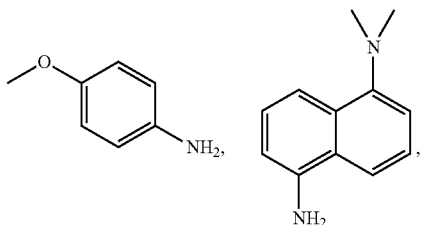

(MOA)          (15DMN)

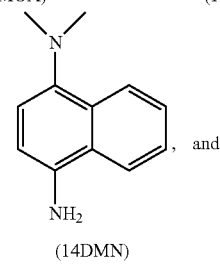

, and (14DMN)

-continued

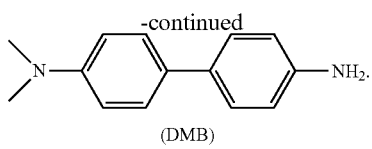

(DMB)

Reaction conditions for the formation of sulfur-reactive moiety 120 are in general between 22° C. and 200° C. in dimethyl sulfoxide (DMSO) (($CH_3)_2SO$) solvent. The solvent used in the formation reaction of the sulfur-reactive moiety 120 may be a polar aprotic solvent. Other potential solvents include, without limitation, acetonitrile, tetrahydrofuran (THF), N,N-Dimethylformamide (DMF), toluene, diethyl ether, propylene carbonate, chloroform, 1,3-Dimethyltetrahydropyrimidin-2(1H)-one (DMPU), 1-Methyl-2-pyrrolidone (NMP), and N,N-Dimethylacetamide (DMAc).

Figure 3:
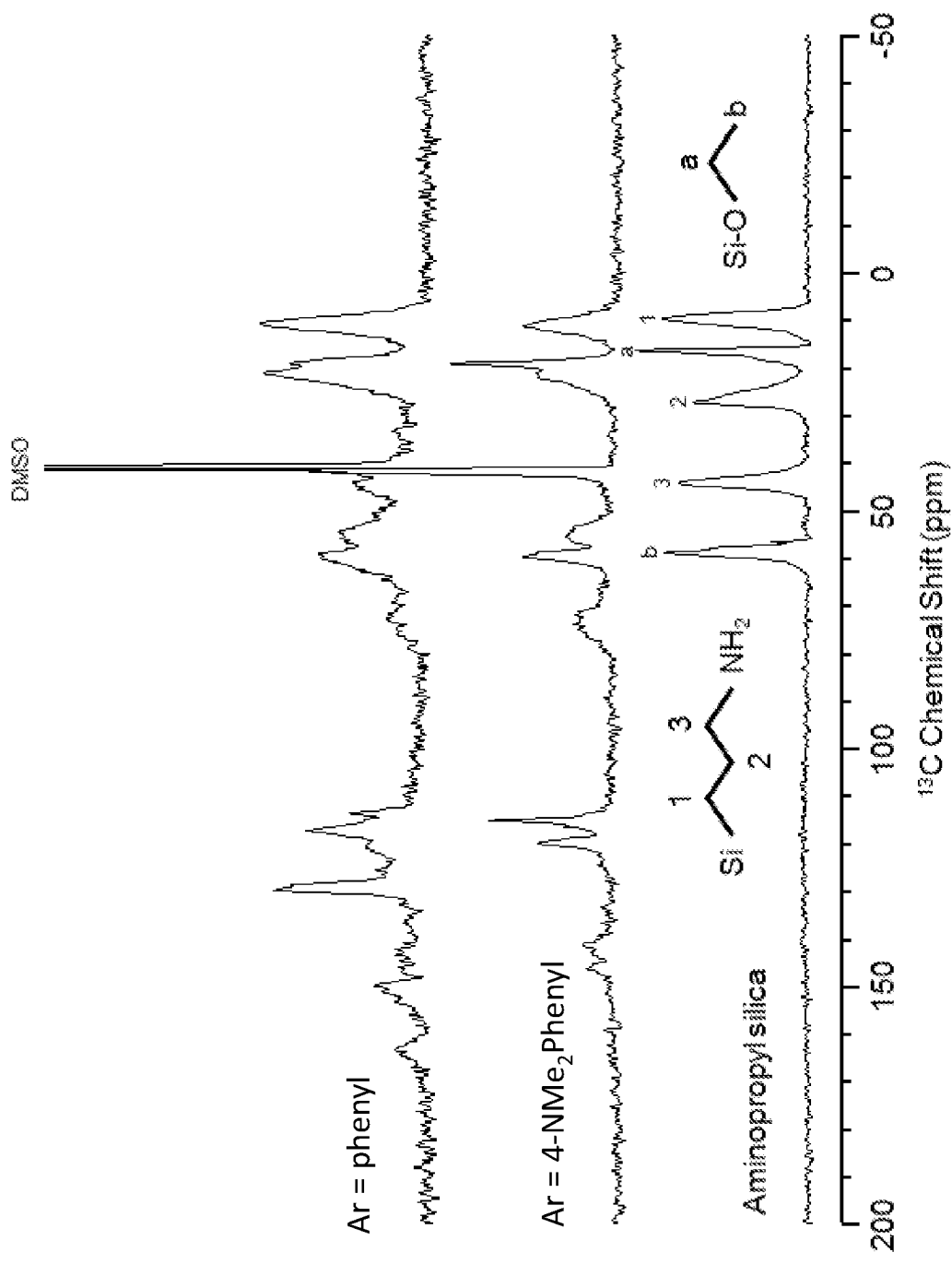
FIG. 3 depicts $^{13}$C-NMR spectra reflecting formation of a surface-modified particle having a moiety that reacts with sulfur compounds produced according to an exemplary reaction scheme.

FIG. 3 depicts $^{13}C$-NMR spectra reflecting formation of a surface-modified particle having a moiety that reacts with sulfur compounds produced according to an exemplary reaction scheme. The particle in this example was silica. The linkage 110 was formed using APTES. Two different particle types were synthesized and evaluated. A first particle type includes a sulfur-reactive moiety 120 wherein "Ar" is a phenyl group and a second particle type includes a sulfur-reactive moiety 120 wherein "Ar" is a N,N-dimethylamino-p-phenyl group. Formation of the hexahydrotriazine moiety in each case was performed in DMSO at 50° C. The NMR spectra establish the formation of hexahydrotriazine surface-functionalized silica particles.

Filtration of Sulfur Compounds

Figure 4:
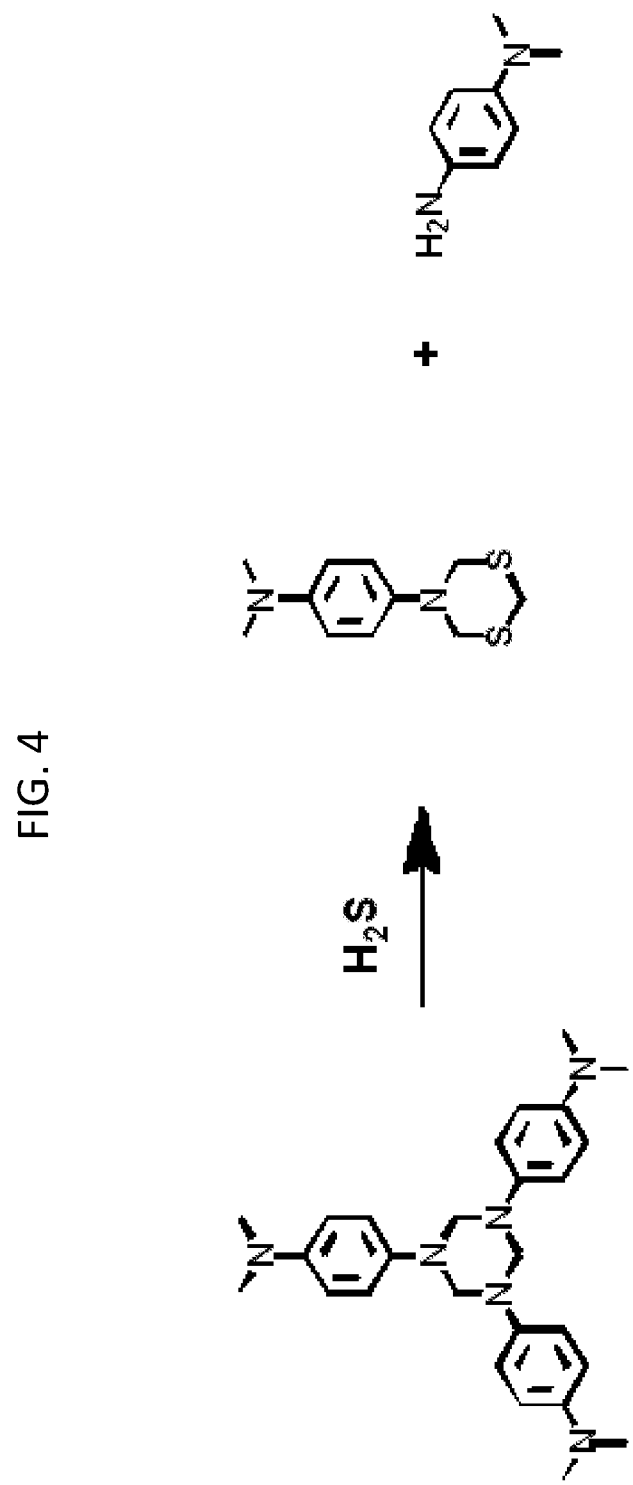
FIG. 4 depicts a reaction between a hexahydrotriazine moiety and a sulfur compound.

With reference now to FIG. 4, a compound including a hexahydrotriazine (HT) moiety may react with a sulfur compound as depicted. In this instance, the sulfur compound is $H_2S$, but thiol compounds will also react with a hexahydrotriazine group. Under some reaction conditions various sulfur allotropes, such as octosulfur ($S_8$, also referred to as cyclo-sulfur), may also react with HT materials.

In the reaction depicted in FIG. 4, the sulfur atoms replace two of three nitrogen atoms in the HT moiety, which results in the substituent attached to the two replaced nitrogen atoms (e.g., phenyl group, N,N-dimethylamino-p-phenyl group, etc.) being separated from (that is, no longer covalently bonded to) the hexahydrotriazine (HT) moiety. In general, reaction of the HT material with a sulfur compound thus results in attachment of sulfur atoms to the surface-modified particle 100. As such, particles 100 can be used as a reactive filtration media to remove sulfur compounds from various fluids.

As a means to understand the reaction between HT functionalized particles and sulfur compounds, studies on small molecule model compounds have been performed. In general, the small molecule model compounds incorporate a hexahydrotriazine group but are not attached to the surface of a particle. Reactions of the small molecule model compounds are typically easier to monitor and detect under controlled conditions than reactions involving surface-modified particles.

Figure 5:
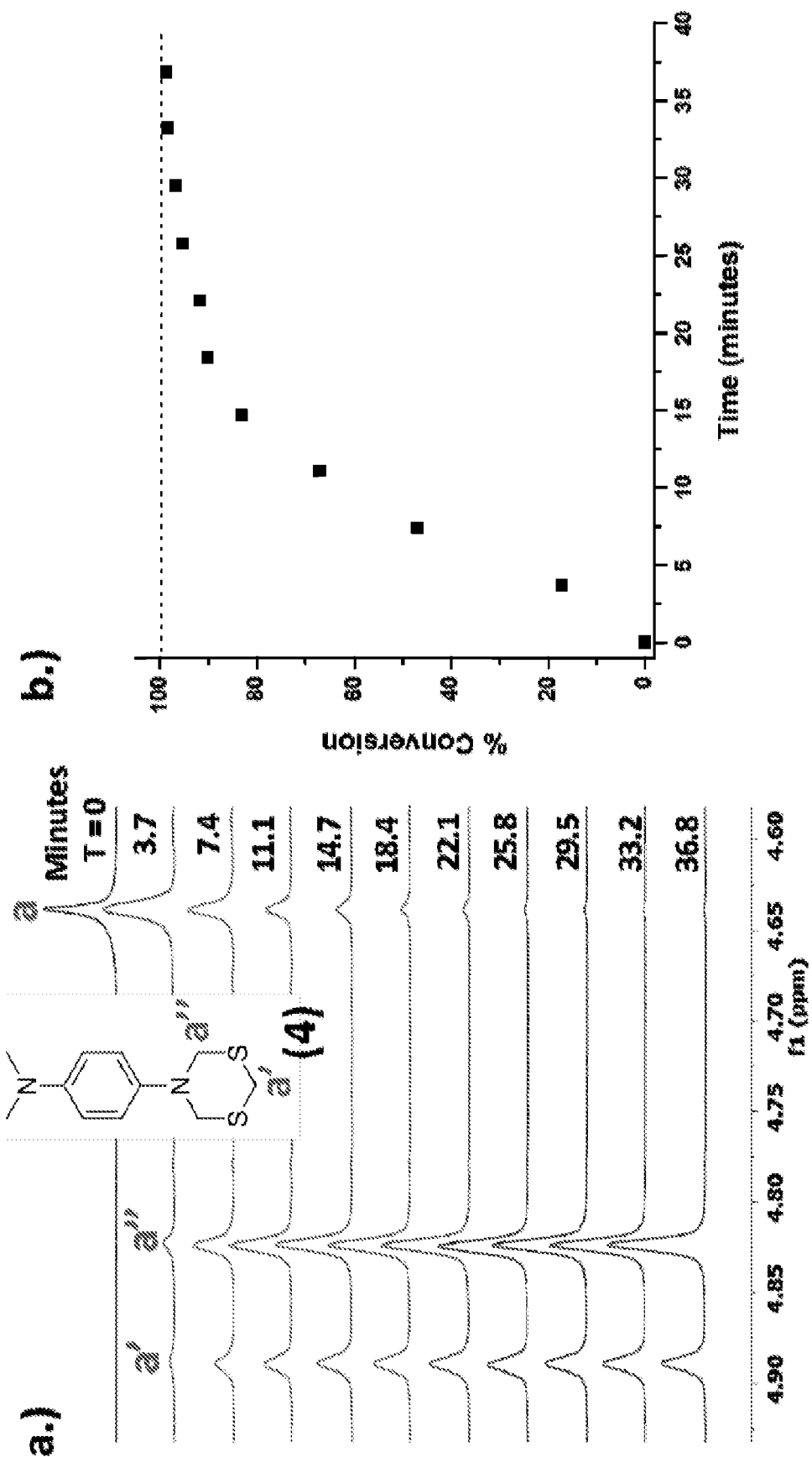
FIG. 5 depicts a) $^1$H-NMR spectra of a reaction of a small molecule model compound having a hexahydrotriazine moiety and a sulfur compound, and b) a kinetic profile of the reaction the small molecule model compound and the sulfur compound.

FIG. 5 depicts $^1H$-NMR spectra of a reaction between a sulfur compound ($H_2S$) and small molecule model compound including a hexahydrotriazine moiety (4,4',4''-(1,3,5-triazinane-1,3,5-triyl)tris(N,N-dimethylaniline)) (also referred to as SMC-HT). FIG. 5 shows several NMR spectra obtained over time (with a 3.7 minute spacing).

In FIG. 5, the diagnostic singlet (a) corresponding to a hydrogen on the nitrogen-rich HT core is observed to decrease in intensity during the course of the reaction, while two new peaks (a') and (a'') increase in intensity. The peaks (a') and (a'') are considered to correspond to the hydrogen atoms on the diothiazine reaction product.

FIG. 5 also depicts the kinetic profile of the reaction between the small molecule compound (SMC-HT) and $H_2S$. The data in the kinetic profile is based on the $^1H$-NMR measurements. After a period of approximately 37 minutes, the peak (a) is no longer observed in the spectrum, indicating substantially complete conversion of SMC-HT into a different compound, specifically a diothiazine compound in which two sulfur atoms have been incorporated in place of two ring nitrogens of the original SMC-HT. The triathiane product (corresponding to a reaction product in which all ring nitrogens in the SMC-HT are replaced with sulfur atoms) has not been observed experimentally under the studied reaction conditions; however, preliminary density functional theory calculations suggest the formation of triathiane is thermodynamically favorable. Based on these preliminary results it is possible the formation of the triathiane product is kinetically disfavored over the two-sulfur (diothiazine) reaction product. In general, it is expected that the sulfur atoms will substitute with the aromatic amines rather than the nitrogen most directly linked to the particle because the electronics of the aryl ring makes the aromatic amine(s) a better leaving group and better able to stabilize the build-up of positive charge on the adjacent carbon atom thought necessary for the sulfur exchanging reaction.

While a reaction between SMC-HT and hydrogen sulfide ($H_2S$) has been evaluated, it is expected that other sulfur compounds would similarly react with a HT moiety.

Removal of Sulfur Compounds from Fluids

As described, HT moieties react with sulfur compounds in such a way that sulfur becomes linked to the surface-modified particles incorporating the HT moiety. Upon reaction with HT moiety, the sulfur becomes attached to the particle via covalent linkages. As such, surface-modified particles incorporating HT moieties can be used as reactive filter media for removal of sulfur compounds from fluids. In various embodiments, such filtration media can be incorporated in a fixed-media filter device such as an air intake filter for microelectronic fabrication facility or other pollution sensitive environment, an automotive fuel filter, an automotive oil filter, a water treatment filter, a combustion exhaust filter, or the like. In this context, a fixed-media filter device could incorporate surface-modified particles incorporating a HT moiety by, for example, filling a cavity with particles, embedding the particles in a binder resin or gel, incorporating the particles in a porous medium, and allowing or causing the particles to gelate or otherwise agglomerate into a mass.

Alternatively, surface-modified particles may be added directly to the fluid from which sulfur compounds are to be removed. The added particles and the fluid may later be separated by various methods, such as, for example, fixed-filter filtration, settling, sedimentation, centrifuge, solvent partitioning, evaporative methods, distillation, or the like. The surface-modified particles may in some embodiments be included in a fluidized bed apparatus—that is, the fluid to be filtered and the surface-modified particles may be contacted with each other under flow and pressure conditions which cause the fluid-particulate mixture to behave similarly to a fluid (fluidize).

Figure 6:
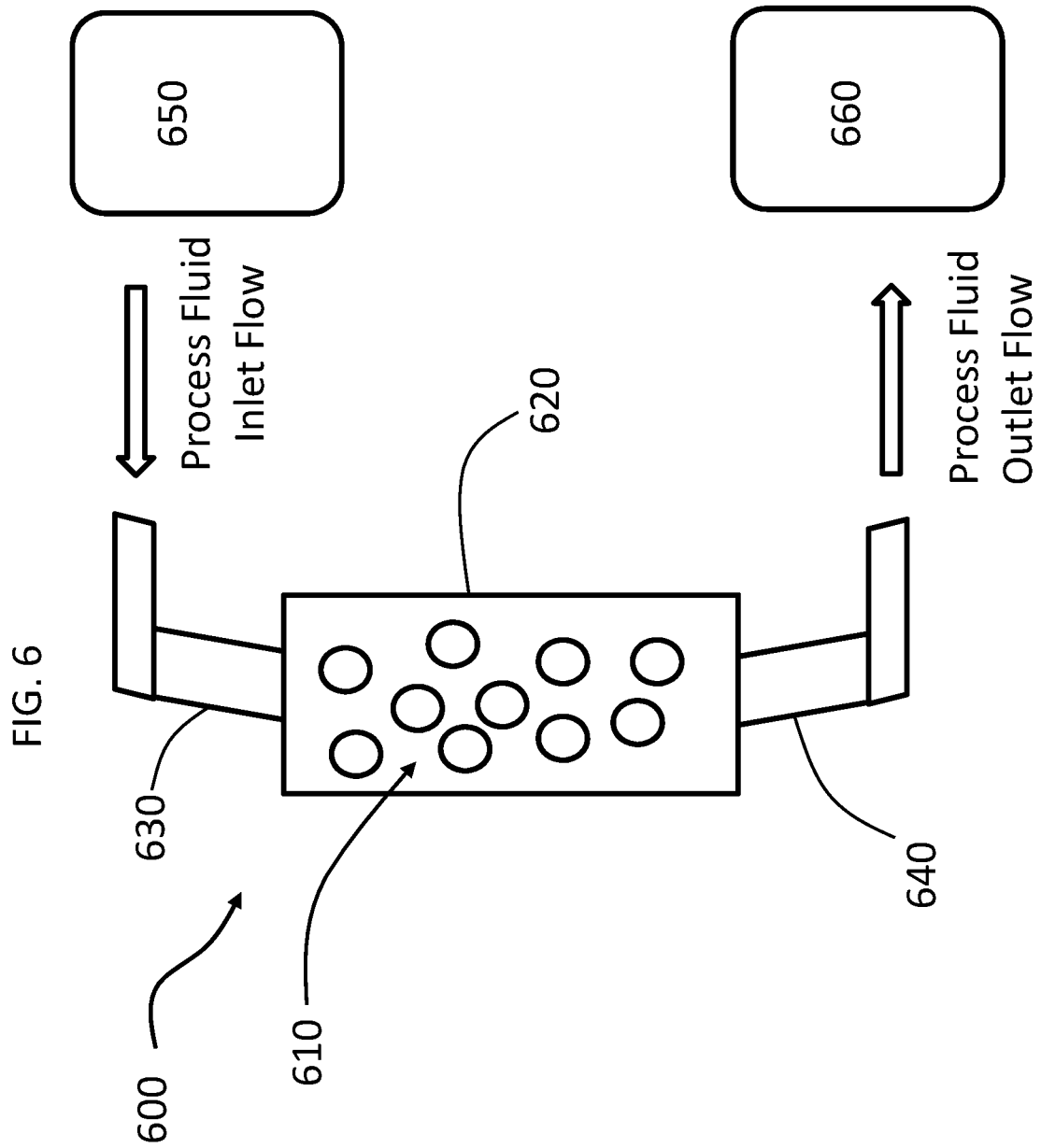
FIG. 6 depicts a filter including a surface-modified particle for removing sulfur compounds from a fluid.

FIG. 6 depicts a filter 600 including filter media 610. Filter media 610 may be comprised of surface-modified particles 100 incorporating a HT moiety. Filter media 610 is disposed in a filter body 620. It should be noted that FIG. 6 is a schematic depiction that is not necessarily to scale and, as such, filter media 610 may be any size relative to filter body 620. Indeed, in various embodiments, filter media 610 may include particles having nano-scale dimensions. Filter body 620 may be packed with filter media 610 or filter media 610 may comprise loose particles which move within filter body 620. Alternatively, a portion of filter body 620 may be packed and a different portion may include loose particles. A filter body 620 packed or filled with particles may provide a filter media 610 having tortuous fluid pathways to promote contact between the fluid and filter media 610.

As depicted, filter 600 receives a fluid from source 650 through process fluid inlet 630. The process fluid includes sulfur compounds and is filtered by contact with filter media 610 within filter body 620. After passing through filter body 620, the fluid is output from process fluid outlet 640 to environment 660.

As noted, filter media 610 may include a surface-modified particle 100 incorporating a HT moiety. Filter media 610 may comprise monodisperse surface-modified particles 100 (particles with approximately the same dimensions or a narrow distribution of sizes). Filter media 610 may alternatively comprise surface modified particles 100 having many different nominal sizes or any statistical distribution of particle sizes. The surface-modified particles 100 may each have the same type of surface functionalization or there may be different types of surface functionalized particles 100. That is, for example, some particles 100 may incorporate phenyl groups and other particles 100 may incorporate N,N-dimethylamino-p-phenyl groups.

Filter media 610 may in some embodiments include particles or material intended to filter fluid components other than sulfur compounds. For example, filter media 610 may incorporate a mesh or fabric to filter macroscopic particles, grit, and dust. Filter media 610 may also incorporate materials which react with or otherwise sequester various dissolved metal components in the process fluid.

Source 650 may be anything that supplies, outputs, generates, or contains a fluid including sulfur compounds. For example, source 650 may be a crude oil reservoir, a natural gas storage basin, a liquefied natural gas (LNG) production facility, a petroleum refinery, petrochemical plant, or the like, which collectively may be referred to as a hydrocarbon processing facility.

Crude oil and natural gas deposits typically contain sulfur compounds such as $H_2S$ and mercaptans at undesirable levels. For crude oils, sulfur compound levels must be lowered during the refining process to meet customer and regulatory requirements for end-use fuels and lubricants. For natural gas, sulfur levels often must be reduced prior to storage or transport because sulfur compounds will promote corrosion of components of pipelines, storage tank, and processing equipment. Sulfur-based air pollution from the combustion of natural gas may also be of concern and require reductions in sulfur levels in natural gas feed stocks prior to combustion.

In some embodiments, source 650 may include a power plant burning hydrocarbon fuel (e.g., natural gas, oil, and coal) which contains sulfur. The power plant outputs combustion exhaust streams including sulfur-based air pollutants such as $H_2S$ found in or derived from the hydrocarbon fuel. Source 650 may similarly be a combustion engine or a boiler found in a vehicle burning hydrocarbon fuels (e.g., gasoline, kerosene, diesel fuel) including sulfur compounds, and thus consequently outputs combustion exhaust streams including sulfur-based air pollutants. In such instances, filter 600 may be referred to as an exhaust gas filter and such a system may be used to reduce sulfur-based air pollutants from in the combustion exhaust gas.

Source 650 may also be a fuel storage tank of a vehicle (e.g., automobile, boat, ship, diesel locomotive, motorcycle, airplane, helicopter, etc.) having a combustion engine or a boiler burning fuels including sulfur compounds. In such instances, filtration system 120 may be referred to as a fuel filter and may serve to reduce air pollution or engine/boiler corrosion by reducing sulfur compound levels in fuels prior to combustion. Similarly, source 100 may be an oil reservoir of a vehicle having an internal combustion engine. In such instances, the filter 600 may be referred to as an oil filter.

Source 650 may also be the open atmosphere. Sulfur-based air pollution on occasion may be at levels which are too high for prolonged exposure by humans, animals, or corrosion sensitive materials such as electronic equipment. In these instances, air handling equipment may incorporate filter 600 to provide clean air to environment 660.

Environment 660 may, in general, be anything receiving the filtered fluid from filter 600. Environment 660 may be the open atmosphere, when, for example, source 650 is a combustion engine or a power plant. When source 650 is the open atmosphere, environment 660 may be a pollution sensitive environment such as a semiconductor device fabrication facility, a microelectronic device manufacturing facility, a data storage center, a server room, a server farm, a electronic component warehouse, a hospital ward, archival storage facility, or portions thereof. When source 650 is a crude oil reservoir or natural gas basin, environment 660 may be, for example, a crude oil storage tank, a refinery, a natural gas storage basin, a LNG processing plant, a pipeline, a petrochemical plant, or portions thereof.

Figure 7:
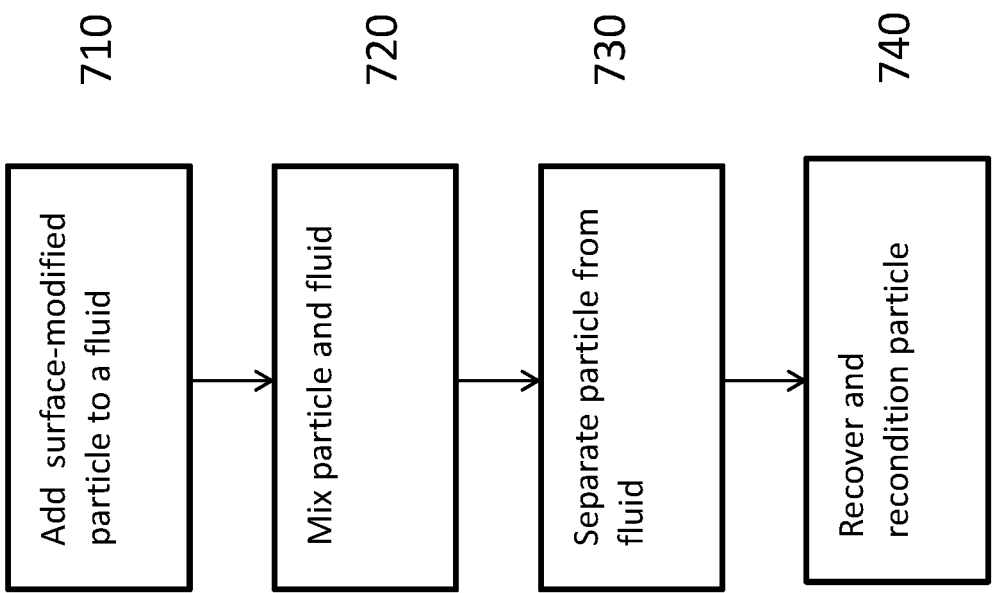
FIG. 7 is a flowchart depicting a first method for removing sulfur compounds from a fluid.

FIG. 7 depicts a method 700 for removing sulfur compounds from a fluid. In element 710 of the method, a surface-modified particle is added to a fluid. The surface-modified particle may correspond to a particle 100 incorporating an HT moiety which reacts with sulfur compounds, as described above.

In element 720 of method 700, the particle may be mixed with the fluid. Element 720 may including stirring the fluid, placing baffles in the fluid flow stream, passing the fluid and particle through in-line mixers, shaking, or otherwise agitating the fluid. Element 720 may be optional in some embodiments and an active mixing/agitation step may be unnecessary.

In element 730, the particle is separated from the fluid. The separation process may involve size-exclusion filters, or the like. Depending on the size of the particle(s) and viscosity of the filtered fluid, it may be possible to use a settling of sedimentation process to the separate the particle (s) from the fluid. Centrifuge systems may also be used, but would be relatively costly for most applications. Additionally, the separation process may be a series of different processes such as size-exclusion filtration after a settling process. Also, evaporative methods and solvent partitioning methods may be incorporated in the separation process. In some embodiments, the separation process may be unnecessary because it may be sufficient to simply bind the sulfur compounds to the surface-modified particle to achieve a beneficial result. For example, when the fluid is a crude oil being prepared for shipment in a pipeline or by a tanker, it may be sufficient for purposes of corrosion prevention to bind the sulfur compounds to the surface-modified particle to reduce the availability of the sulfur contaminants in corrosive reactions.

In an example embodiment, the fluid to be filtered may be contained in a storage tank or reaction vessel and a surface-modified particle could simply be dumped into the tank or vessel. Depending on size and fluid density it may be advantageous to physically mix or stir the fluid. Once the particle as been placed in contact with the fluid, sulfur sequestering reactions will occur as described previously and sulfur will be bound to particulate filtration media.

In element 740 of the method, the surface-modified particle may be recovered and reconditioned if desired. After separation of the particle from the process fluid, the particle may be recovered, that is, for example, separated from size-exclusion filter by back-flushing the filter. The reconditioning process of the particle involves reformation of the HT surface functionalization by removal of the previously incorporated sulfur atoms under acidic conditions and then reaction with an HT precursor.

Figure 8:
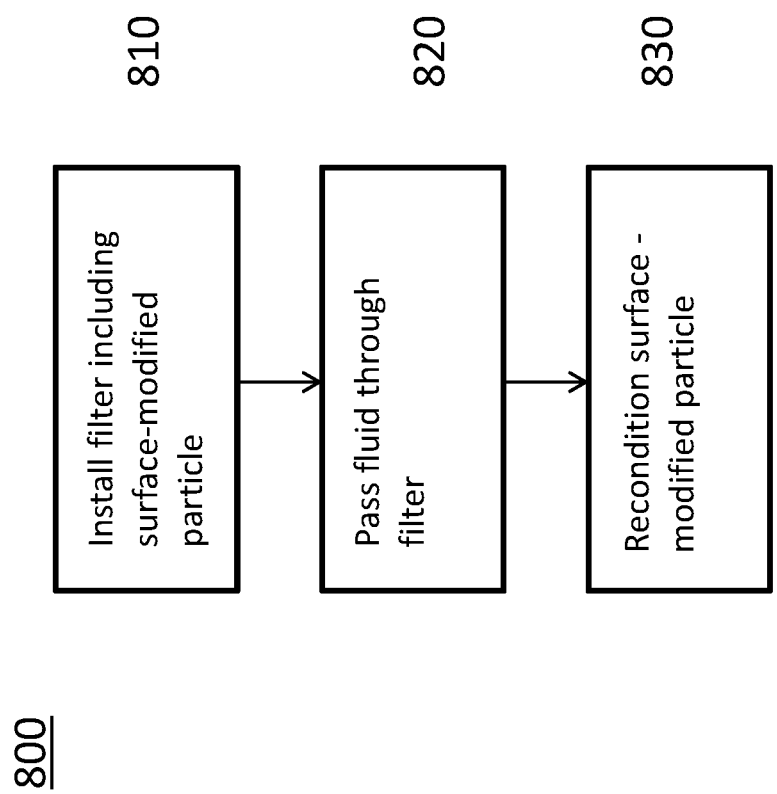
FIG. 8 is a flowchart depicting a second method for removing sulfur compounds from a fluid.

FIG. 8 depicts a method 800 for removing sulfur compounds from a fluid. In an embodiment of method 800, a filter including a surface-modified particle is installed (element 810). In an example embodiment of method 800, the filter may correspond to filter 600.

In element 820 of the method 800, the fluid is passed through the filter. The fluid including a sulfur compound contacts the at least one surface-modified particle including a HT moiety (e.g., surface-modified particle 100) within the filter. The particle reacts with the sulfur compound and the sulfur compound is thereby bound to the particle and removed from the fluid. Element 820 may require pumps, gas compressors, or similar equipment to provide a necessary pressure differential between the intake point and the output point of the installed filter to induce fluid flow through the filter. The heating or cooling of the fluid may also be necessary, depending on the source of the fluid. For example, combustion exhaust gas from a power plant may initially be at a very high temperature and it may be preferable to reduce the temperature before passing the fluid through the filter.

In element 830 of the method 800, the surface-modified particle may be reconditioned. The reconditioning process of the particle involves reformation of the HT surface functionalization by removal of the previously incorporated sulfur atoms and reaction with an HT precursor, for example, exposing the particle to acidic conditions.

It should be noted that a particle may be incorporated into or be a portion of a coating of a substrate. That is, specifically, a surface-modified particle of various embodiments of the present disclosure may be incorporated into or be a portion of a coating of a substrate. A plurality of surface-modified particles according to various embodiments may form a coating on a substrate. A substrate in this context may be, for example, an interior surface of a pipe, an exterior surface of a pipe, a countertop, a surface of a storage tank, a microelectronic component, a silicon wafer, a printed circuit board, or portions of the foregoing.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

While the foregoing is directed to embodiments of the present invention, other and further embodiments of the invention may be devised without departing from the basic scope thereof, and the scope thereof is determined by the claims that follow.

What is claimed is:

1. A surface-attached molecule, comprising:

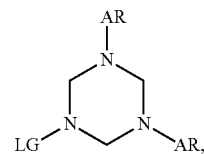

wherein:
LG is a linking group covalently bonded to a nitrogen atom of a hexahydrotriazine moiety and a surface, and
AR is an electron-donating group.

2. The surface-attached molecule of claim 1, wherein the electron-donating group includes an aromatic moiety.

3. The surface-attached molecule of claim 1, wherein the electron-donating group is a N,N-dimethylamino-p-phenyl group.

4. The surface-attached molecule of claim 1, wherein the electron-donating group is a phenyl group.

5. The surface-attached molecule of claim 1, wherein the electron-donating group is one of a methyl ether, a pyrene, a hydroxyl group, a sulfhydryl group, or an alkylthio group.

6. The surface-attached molecule of claim 1, wherein the linking group is a straight-chain alkyl group including at least three carbon atoms.

7. The surface-attached molecule of claim 1, wherein the linking group is an alkyl silyl group.

8. The surface-attached molecule of claim 7, wherein the alkyl silyl group is a propyltriethoxysilyl group.

9. The surface-attached molecule of claim 1, wherein AR is at least one of the following:

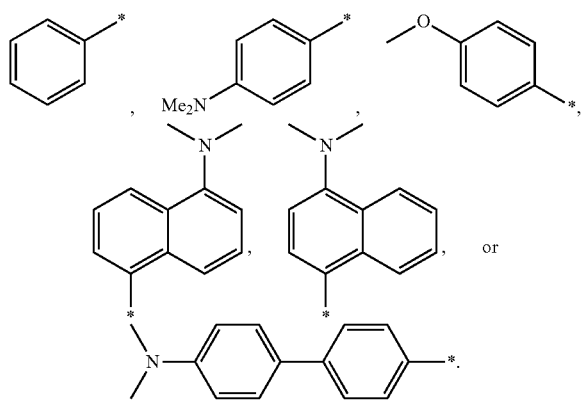

10. The surface-attached molecule of claim 1, wherein the surface is an outer surface of a silica particle.

11. A surface-attached molecule, comprising:

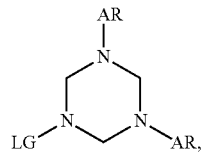

wherein:
LG is a linking group covalently bonded to a nitrogen atom of a hexahydrotriazine moiety and a surface, and
AR is an electron-donating group, the electron-donating group comprising an aromatic moiety.

12. The surface-attached molecule of claim 11, wherein the electron-donating group is a N,N-dimethylamino-p-phenyl group.

13. The surface-attached molecule of claim 11, wherein the electron-donating group is a phenyl group.

14. The surface-attached molecule of claim 11, wherein the linking group comprises a straight-chain alkyl group including at least three carbon atoms.

15. The surface-attached molecule of claim 11, wherein the linking group comprises an alkyl silyl group.

16. The surface-attached molecule of claim 15, wherein the alkyl silyl group is a propyltriethoxysilyl group.

17. The surface-attached molecule of claim 11, wherein AR is at least one of the following:

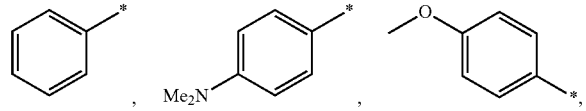

-continued

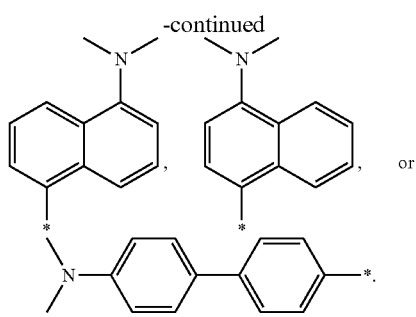

18. The surface-attached molecule of claim 11, wherein the surface is an outer surface of a silica particle.

19. A surface-attached molecule, comprising:

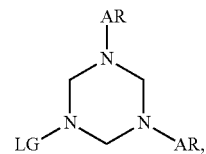

wherein:
LG is a linking group covalently bonded to a nitrogen atom of a hexahydrotriazine moiety and a surface, wherein the linking group comprises a straight-chain alkyl group having at least three carbon atoms, and
AR is an electron-donating group, the electron-donating group comprising an aromatic moiety.

20. The surface-attached molecule of claim 19, wherein the surface is an outer surface of a silica particle.

* * * * *